United States Patent [19]
Dyrud et al.

[11] Patent Number: 5,609,164
[45] Date of Patent: Mar. 11, 1997

[54] METHOD OF FORMING AN EARPLUG CONTAINMENT DEVICE

[75] Inventors: James F. Dyrud, New Richmond, Wis.; Gerald V. Elstran, Woonsocket, S. Dak.; Paul E. Olson, Stillwater, Minn.

[73] Assignee: Minnesota Mining and Manufacturing Company, St. Paul, Minn.

[21] Appl. No.: 547,062

[22] Filed: Oct. 23, 1995

[51] Int. Cl.$^6$ .................................................. A61F 11/00
[52] U.S. Cl. ............................ 128/864; 128/865; 128/897
[58] Field of Search .................................. 128/846, 859, 128/864–867; 181/129, 130, 135

[56] References Cited

U.S. PATENT DOCUMENTS

| | | | |
|---|---|---|---|
| Re. 29,487 | 12/1977 | Gardner, Jr. | 128/152 |
| 2,393,340 | 1/1946 | Russell | 128/864 |
| 4,158,087 | 6/1979 | Wood | 521/137 |
| 4,160,449 | 7/1979 | Wade | 128/152 |
| 4,219,018 | 8/1980 | Draper, Jr. | 128/152 |
| 4,321,998 | 3/1982 | Van de Walker et al. | 206/229 |
| 4,579,112 | 4/1986 | Scott | 128/151 |
| 4,774,938 | 10/1988 | Leight | 128/864 |
| 4,880,076 | 11/1989 | Ahlberg et al. | 181/130 |
| 5,002,151 | 3/1991 | Oliveira et al. | 181/130 |
| 5,044,463 | 9/1991 | Carr | 128/864 |
| 5,188,123 | 2/1993 | Gardner, Jr. | 128/864 |
| 5,195,539 | 3/1993 | Dyrud | 128/864 |
| 5,483,027 | 1/1996 | Krause | 128/865 |

OTHER PUBLICATIONS

"6300 Disposable Earplugs," Product literature from 3M.
L. H. Smokak, B. F. Iserman, and R. W. Hawkinson, "Disposable Foam Earmolds," Reprint from *Hearing Instruments*, vol. 38, No. 12 (1987).
E–A–R Division product literature on E–A–R Plugs.
N. L. Carter and G. Upfold, "Comparison of Earphone and Sound Field Methods for Estimating Noise Attenuation of Foam Earplugs," *Am. Ind. Hyg. Assoc. J.*, 54(6) pp. 307–312 (1993).
P. Hellstrom and A. Axelsson, "Miniature Microphone Probe Tube Measurements In The External Auditory Canal," *J. Acoust. Soc. Am*, 93(2) pp. 907–919 (Feb. 1993).

*Primary Examiner*—Michael A. Brown
*Attorney, Agent, or Firm*—Gary L. Griswold; Walter N. Kirn; James A. Rogers

[57] ABSTRACT

A method for forming an earplug containment device comprising providing at least one thin-walled, hollow sleeve having an inside diameter less than the diameter of the human ear canal, compressing a slow-recovery earplug having a diameter greater than that of the human ear canal to a cross-sectional size less than that of said sleeve, and inserting said compressed earplug into said sleeve.

7 Claims, 2 Drawing Sheets

5,609,164

METHOD OF FORMING AN EARPLUG CONTAINMENT DEVICE

FIELD OF THE INVENTION

The invention relates to an earplug containment device and a method for preparing earplugs for use.

BACKGROUND OF THE INVENTION

Foam earplugs have been generally well accepted for providing sound attenuation. Such earplugs are generally cylindrical in shape and of somewhat larger diameter than the human ear canal. The earplugs may be composed of a foamed plasticized polymeric material having a sufficiently high concentration of plasticizer to provide the earplug with a reduced rate of recovery from compression. The earplugs can be compressed by twirling lengthwise between the fingers. The compressed earplug is inserted into the ear canal where it then recovers slowly until it conforms to and obturates the ear canal, thus suppressing or attenuating the transmission of noise.

To aid in compression of earplugs, an earplug may be encased in an envelope of thin flexible plastic material which extends lengthwise beyond the end of the earplug. The envelope is twistable to compress the earplug and thereby reduce its size to facilitate introduction of the earplug into the ear canal. The envelop can be open to the atmosphere to permit air to be expelled when the envelop is compressed and twisted, or the envelop can be sealed and evacuated.

Earplugs have been provided as units with an inserter and tie which can be worn as a unit. The earplugs having a relatively flexible stem and adjacent spaced flanges of varying size made of relatively soft, yieldable, resilient material which readily conform to the ear canal. Each earplug has outer end attached to a tie member on which is slideably carried and retained an earplug inserter. The earplug inserter is movable from a carrying position into engagement with the outer end of an earplug for its insertion into the ear canal.

A combined protective case and inserter for earplugs having flanges has been disclosed. The case includes cover which can be held in a closed or an open position. The cover can be positioned such that either one of two earplug inserting means are exposed for aiding in insertion of the earplug into a users ear.

An earplug compression device for slow recovery earplugs is also known. The device has a flexible strip and a base, the flexible strip being fastened at one end to the base with the other end passing through a slot in the base to form a tubular compression means. An earplug is placed within the device and tension is applied to the unattached end of the flexible strip to compress the earplug for insertion in an ear canal.

SUMMARY OF THE INVENTION

The present invention provides an earplug containment device for slow-recovery earplugs comprising a thin-walled, hollow sleeve having an inside diameter less than the diameter of a human ear canal and at least one slow recovery earplug maintained in a compressed state and positioned within said sleeve, said earplug being capable of expanding to a diameter greater than that of the human ear canal. Preferably, a short length of the earplug protrudes beyond the end of the sleeve and forms a bulbous portion which has a diameter greater than that of the human ear canal.

The present invention further provides a method for preparing an earplug ready for use comprising providing a containment device comprising a thin-walled, hollow sleeve having an inside diameter less than the diameter of the human ear canal, compressing a slow-recovery earplug having a diameter greater than that of the human ear canal to a cross-sectional size less than that of the sleeve and inserting the compressed earplug into the sleeve.

The earplug containment device of the present invention may comprise only a sleeve or it may comprise a multiplicity of sleeves. The device provides a means for ensuring that the slow-recovery earplug is properly compressed prior to insertion in the ear canal. The sleeve, as well as compressing the earplug, provides a cover for that part of the earplug contained within the sleeve ensuring cleanliness of the earplug. The earplug is substantially cylindrical, e.g., bullet shaped, and can have a shallow taper toward the insertion end to conform more readily to the inward taper of the ear canal.

DETAIL DESCRIPTION OF THE INVENTION

Figure 1:
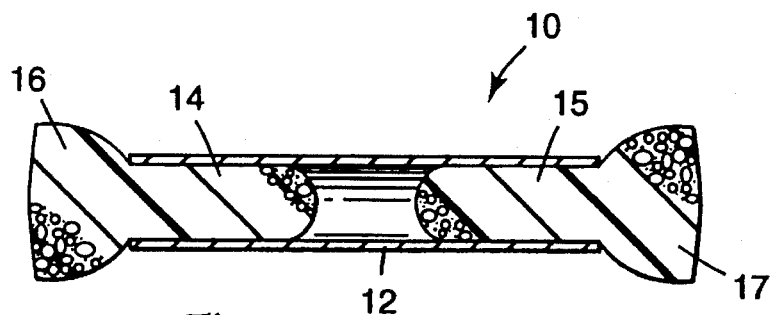
FIG. 1 is a cross-sectional view of a containment device of the invention.

The sleeve of the containment device of the present invention is a thin-walled, hollow sleeve which is generally tubular in configuration. The wall of the sleeve preferably is as thin as possible while reliably retaining one or two earplugs. The sleeve preferably has an inner surface having a low coefficient of friction to permit easy removal of the slow-recovery earplug. The inner surface of the sleeve may be cylindrical or tapered to a shape matching the inward taper of the human ear canal.

The sleeve may be formed, for example, from a thermoplastic material which can be extruded in a seamless tubular form. Useful thermoplastic sleeves are preferably from 0.1 to 0.5 mm, more preferably about 0.25 mm, in thickness. The sleeve may also be formed of helically wound strips of plastic-coated paper. Useful paper sleeves are preferably from 0.2 to 1 mm, more preferably about 0.5 mm, in thickness. Biodegradable papers may be preferred because of environmental concerns.

The inside diameter of the sleeve should be sufficiently less than the diameter of the human ear canal to compress the earplug to less than the diameter of the ear canal. The average adult ear canal has a diameter of about 9 mm although adult ear canals may have diameters as small as about 5 mm. Therefore, the inside diameter of the sleeve is preferably less than about 7 mm, more preferably less than about 6 mm, most preferably less than about 5 mm.

The slow-recovery earplugs useful in the present invention are generally formed from polymeric foam materials and are well known to those skilled in the art. The earplug must be sufficiently compressible that it can be contained with in the sleeve in its compressed form and sufficiently resilient that it will expand to fit an ear canal. Such earplug materials are disclosed, for example, in U.S. Pat. No. RE. 29,487 (Gardner, Jr.), U.S. Pat. No. 4,774,938 (Leight) and U.S. Pat. No. 4,158,087 (Wood), each of which is incorporated by reference herein.

The earplugs can be inserted into the sleeve of the containment device in a clean environment and removed in a dirty, high noise environment without contaminating the surface of the earplug during removal from the sleeve and insertion into the ear of the user. Preferably, the earplug is inserted into the sleeve as part of the manufacturing process during packaging operations and maintained in the compressed state until used.

To ensure that the earplug remains snugly in place after being inserted into an ear canal, the diameter to which it fully recovers after removal from the hollow sleeve should be slightly larger than the diameter of the human ear canal. For the great majority of wearers, that portion of the earplug that is compressed within the hollow sleeve preferably recovers freely to an average diameter of at least about 10 mm, more preferably at least about 12 mm, most preferably at least about 15 mm.

The compressed portion of the earplug should be elongated and of sufficient length to extend beyond the ossio-tympanic junction of the ear canal without contacting the eardrum. The compressed portion is preferably about 15 to 25 mm, more preferably about 17 mm, in length. When the inserted earplug extends beyond the ossio-tympanic junction of the ear canal and is left in place for an appreciable length of time, that portion which contacted the ossio-tympanic junction exhibits a tiny depression immediately after removal from the ear canal.

Preferably, a short length of the earplug protrudes beyond the end of the sleeve and forms a bulbous portion which has a diameter greater than that of the human ear canal. The bulbous portion is useful for removing the earplug from the sleeve, inserting the earplug into the ear canal, and removing the earplug from the ear canal after use. The bulbous end can prevent insertion of the earplug too far into the ear canal and can serve as an indication that the desired length of the earplug has been inserted. By using the bulbous end as a handle, the compressed portion of the earplug remains untouched and uncontaminated by the user's fingers. The bulbous end preferably comprises from 20 to 40% of the total length of the earplug.

To keep the device of the invention clean, the device can be sealed within a package such as a heat-sealed envelope of plastic film. If desired, the package can be formed to compress the portion of the earplug that protrudes beyond the open end of the hollow sleeve to the same diameter as the inside diameter of the hollow sleeve. Alternatively, the bulbous end may be enclosed and compressed by a cap or peel-away strip which can be removed prior to use to allow the expansion of the bulbous end. The act of opening the package permits the protruding portion to expand to form a bulbous end.

The present invention is further described as follows with reference to the drawings.

In FIG. 1, containment device 10 of the invention includes a thin-walled, hollow, cylindrical sleeve 12 that is open at both ends. Compressed within the sleeve is a portion of each of two bullet-shaped, slow-recovery foam earplugs 14 and 15, the other portions of which protrude beyond an open end of the sleeve to form bulbous ends 16 and 17, respectively. By grasping a bulbous end between the fingertips, each earplug can be pulled from sleeve 12 and inserted into the ear canal before the compressed portion recovers to a size larger than the ear canal. The bulbous end can also function to limit the extent to which the compressed portion of the earplug can be inserted into the ear canal.

To insert an earplug into the sleeve 12, it can be compressed between two flat plates and then compressed laterally by a rectangular piston. From its consequently rectangular shape, it slowly expands against the sleeve to form a cylindrical portion and a bulbous end may form from any non-inserted portion of the ear plug.

Figure 2:
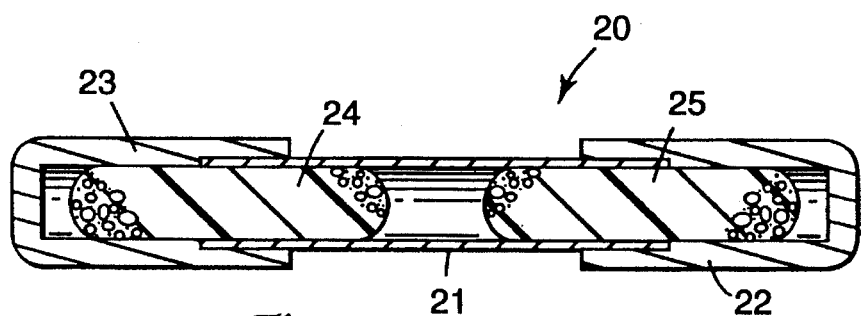
FIG. 2 is a cross-sectional view of a containment device of the invention.

In FIG. 2, containment device 20 of the invention includes thin-walled, hollow, cylindrical sleeve 21, the open ends of which are closed by a pair of caps 22 and 23 that are detachably removable in the axial direction. Compressed within the sleeve and caps are two bullet-shaped, slow-recovery earplugs 24 and 25. When each cap is removed to expose about 20–40% of the length of one of the earplugs, the exposed portion can expand to form a bulbous end (not shown) by which the earplug can be grasped with the fingertips for insertion into the ear canal.

Figure 3:
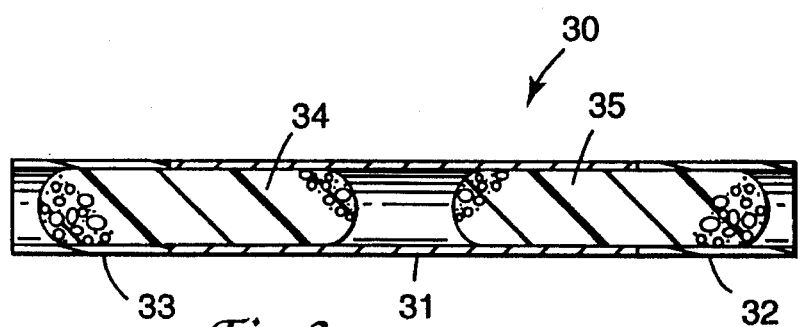
FIG. 3 is a cross sectional view of a containment device of the invention.

In FIG. 3, containment device 30 of the invention includes a thin-walled hollow cylindrical sleeve 31, at each end of which are peel-away strips 32 and 33. Compressed within the sleeve and peel-away strips are two bullet-shaped, slow-recovery earplugs 34 and 35. By peeling way each of the strips, a portion of an earplug is exposed and can expand to form a bulbous end (not shown) by; which the earplug can be grasped with the fingertips for insertion into the ear canal. The small, uniform outer diameter of sleeve 31 and peel-away strips 32 and 33, permits a larger number of containment devices 30 to be stored in a smaller space than is possible with containment devices 10 of FIG. 1.

Figure 4:
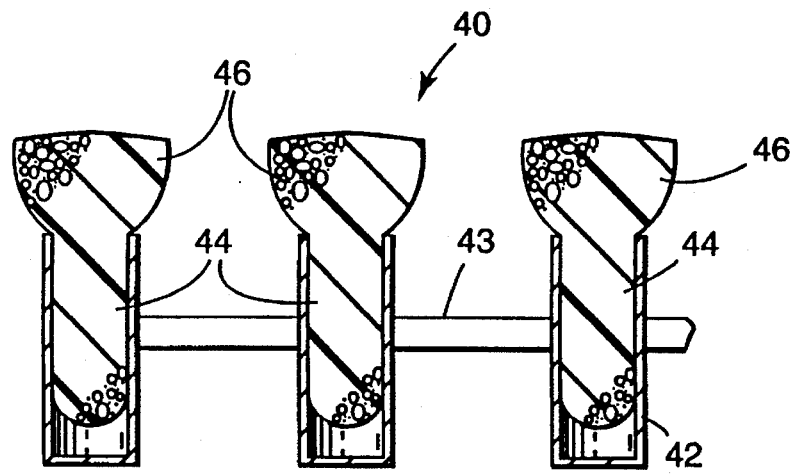
FIG. 4 is a cross sectional view of a portion of a containment device of the invention.

In FIG. 4, containment device 40 of the invention includes a plurality of thin-walled, hollow, cylindrical sleeves 42, each of which is open at only one end. Sleeves 42 are interconnected by a flexible web 43. Compressed within each sleeve is a portion of one bullet-shaped, slow-recovery earplug 44, the other portion of which protrudes beyond the open end of the sleeve to form a bulbous end 46.

Figure 5:
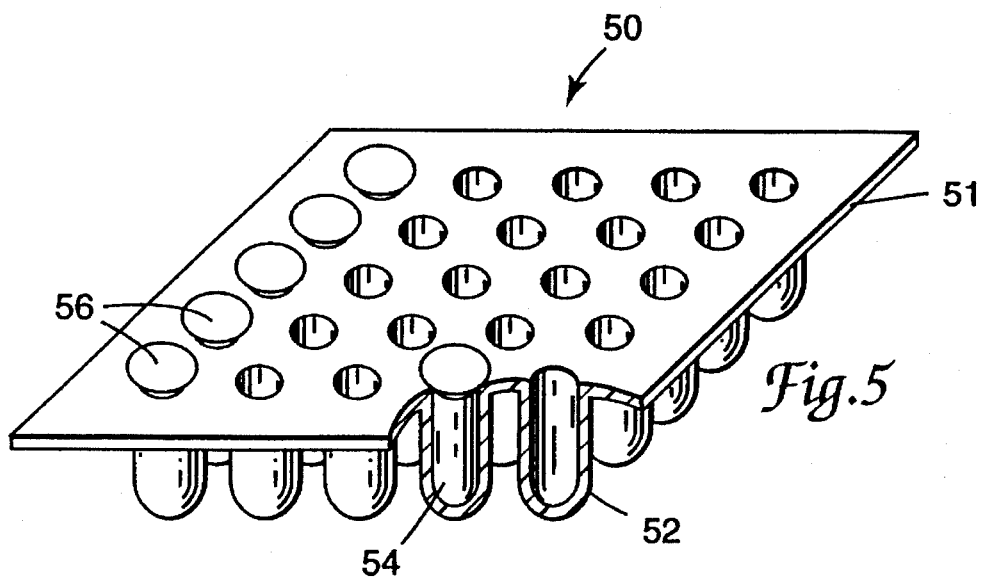
FIG. 5 is a perspective view of a fifth device of the invention.

In FIG. 5, containment device 50 of the invention has a broad web 51 formed with a large number of hollow cylindrical sleeves 52. Compressed within each of the sleeves is a portion of a bullet-shaped, slow-recovery earplug 54, the other portion of which forms a bulbous end 56. The web 51 can be formed as a continuous plastic strip which may be cut into convenient lengths.

Figure 6:
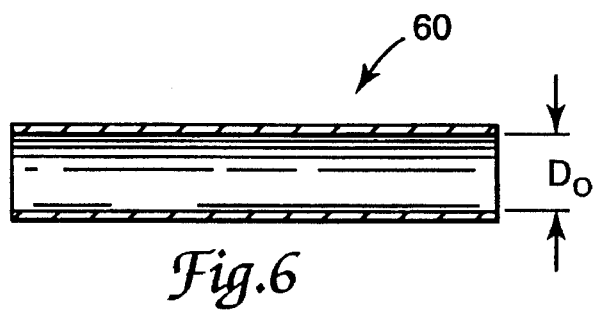
FIG. 6 is a cross sectional view of a compression sleeve useful in the invention.

Each of the sleeves of the containment devices illustrated in FIGS. 1–5 can be a straight cylindrical sleeve 60 as shown in FIG. 6. The sleeve diameter, $D_s$, can vary in size to adapt the size of the earplug to varying sizes of ear canals. Preferably the straight sleeve is about 1 mm smaller, more preferably about 1.5 mm smaller, most preferably about 2 mm smaller, in diameter than the ear canal of the earplug wearer. The smaller the diameter of the sleeve, the broader the range of earplug wearers that can comfortably insert the compressed earplug. Thus, for a small adult ear canal of about 5 mm, the sleeve is preferably about 4 mm in diameter. An earplug compressed to this diameter can also be comfortably inserted in the ear canal of an adult having an average ear canal diameter of about 9 mm, but the time for the earplug to expand to fill the ear canal will be longer than for the wearer with the smaller ear carnal.

Figure 7:
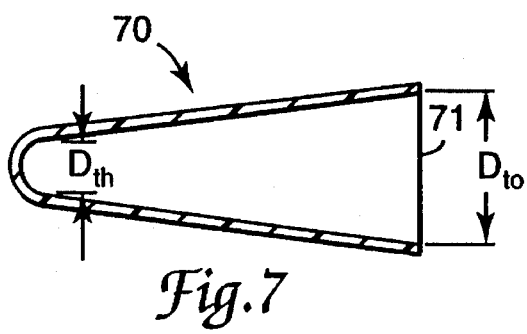
FIG. 7 is a cross sectional view of another compression sleeve useful in the invention.

Each of the sleeves of the containment devices illustrated in FIGS. 1–5 can also be made as a tapered sleeve as shown in FIG. 7. The tapered sleeve 70 has a maximum diameter, $D_{to}$, at open end 71 and a smaller diameter, $D_{th}$, at the opposing hemispherical end 72. Preferably, the difference in diameter between $D_{to}$ and $D_{th}$ is about 1.5 to 3 mm, more preferably about 1.6 to 1.8 mm. The average diameter of the tapered sleeve can vary to adapt the size of the earplug to varying sizes of ear canals. Preferably the average diameter of the tapered sleeve is about 2 mm smaller, more preferably about 1.2 mm smaller, and it can be about 0.4 mm smaller, in diameter than the ear canal of the earplug wearer. Generally, the open end has a diameter of less than about 9 mm, more preferably less than about 7 mm. As with the straight sleeve, a tapered sleeve having a smaller average diameter provides earplugs with more universal comfort in insertion, but requires a longer period of time to expand to fill a larger ear canal.

Preferably, that portion of the sleeve into which the earplug is to be inserted is at least about 15 mm long, more preferably at least about 20 mm long, most preferably at least about 25 mm long. Therefore, sleeves of the containment devices shown in FIGS. 1, 2 and 3 are preferably at least about 30 mm long, more preferably at least about 40 mm long, most preferably at least about 50 mm long.

Figure 8:
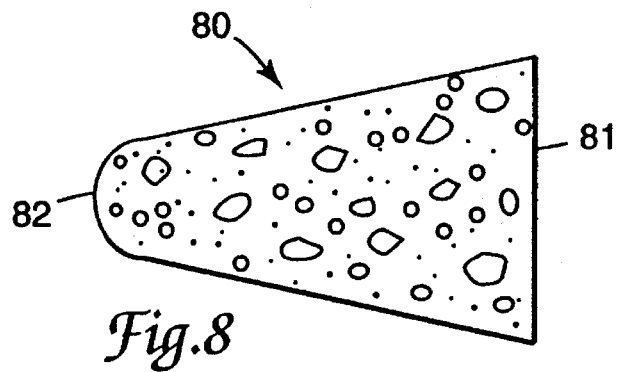
FIG. 8 is a cross sectional view of an earplug useful in the invention.

Preferably, earplugs for use with the containment devices of the present invention are tapered, bullet-shaped earplugs as shown in FIG. 8. Earplug 80 has a flat end portion 81 and a hemispherical end portion 82. To accommodate the great majority of wearers the average diameter of the earplug is preferably about 12 to 14 mm, more preferably at least about 13 mm. The earplug preferably expands to fill the wearer's ear canal in less than about two minutes from the time of removal of the compressed earplug from the sleeve including insertion time into the ear canal and expansion time within the ear canal. To accommodate various ear canal sizes, earplugs can be provided in various sizes, for example, the diameter of the flat end portion can be 15 mm with the hemispherical end portion having a diameter of 11 mm, the diameter of the flat end portion can be 14 mm with the hemispherical end portion having a diameter of 10 mm, or the diameter of the flat end portion can be 16 mm with the rounded end portion having a diameter of 12 mm.

Straight cylindrically earplugs are also useful with the containment devices of the present invention. The earplugs in their expanded form can range in diameter from about 10 mm to 16 mm and can be provided in various sizes to accommodate various sizes of ear canals. Typical diameters for the straight cylindrical earplugs are 12 mm, 13 mm and 14 mm.

Objects and advantages of this invention are further illustrated by the following examples, but particular materials and dimensions thereof recited in these examples, as well as other conditions and details, should not be construed to unduly limit this invention. All parts and percentages in the examples are by weight unless otherwise indicated.

In the examples, noise attenuation performance was tested as follows:

A test subject is seated within a hearing testing sound chamber, facing an operator who administers the test using hearing aid fitting equipment, 3M Master-Fit™ System-Real Ear Measures, available from 3M Hearing Health Care, St. Paul Minn. Broad band noise is broadcast from a speaker located 45° from the frontal axis of the test subject to the test ear side at a distance of one meter. Measurement of sound pressure level as a function of frequency within the ear canal is made using the probe tube microphone of the Master-Fit™ System. Steps of the test procedure are as follows:

1. The size of the ear canal of the subject is determined using tapered probes having various diameters which are inserted into the subject's ear canal to determine the size of the ear canal at the ossio-tympanic junction.
2. The probe tube of the ear measurement device which is connected to the test instrument is positioned in the ear canal without an ear plug inserted.
3. Broad band noise is activated at 65 dB sound pressure level and the base line sound pressure level within the ear canal is recorded.
4. The test operator removes an ear plug form the sleeve of the containment device and inserts the ear plug into the ear canal of the test subject.
5. The time required for the sound pressure level in the ear canal at the center of the hearing frequency band, i.e., 2000 to 5000 Hz, to be reduced by 10 dB is reported.

EXAMPLE 1

A device as shown in FIG. 1 was made using a thin-walled, shape-retaining, hollow cylindrical sleeve of high density polyethylene having a thickness of 0.2 mm, an inside diameter of 6 mm, and a length of 41 mm. Slow-recovery earplugs were molded from a foam material prepared from 29 parts polypropylene glycol (molecular weight about 1000), 28 parts tetrol of pentaerythritol and propylene oxide (molecular weight about 500), 41 parts isocyanate prepolymer (66.3% toluene diisocyanate, 17.5% polypropylene glycol, 16.2 % tripropylene glycol), 0.84 parts surfactant, 0.56 parts stannous octoate catalyst, 0.22 parts pigment, and 0.45 parts water. Each earplug was molded as a bullet shaped tapered form as shown in FIG. 8. The earplug was 25 mm long with a flat end portion being 15 mm in diameter and the rounded end portion being 11 mm in diameter.

Earplugs were mechanically compressed to rectangular blocks having a square cross-section 4 mm on each side. The blocks were inserted into the sleeve with the spherical tips facing inward. A portion about 17 mm of the length of each earplug was contained within the sleeve leaving about 7 mm (30%) extending from the sleeve to form a bulbous end. The earplugs were allowed to remain in the sleeve until expanded to fill the sleeve.

An earplug was removed from the sleeve by grasping the protruding bulbous end between the fingertips and was inserted into a human ear canal, after which the compressed portion gradually expanded to snugly fit into the ear canal. The earplug was removed after 30 minutes and a tiny depression in the compressed portion of the earplug evidenced that it had extended beyond the ossio-tympanic junction of the ear canal.

Ear plugs which had been stored at 22° C. for two years in the containment devices were tested for sound pressure level reduction using six test subjects with three earplugs tested for each subject. The test subjects' ear canal size and the time for sound pressure level reduction (SPLR) by 10 dB are set forth in Table 1.

TABLE 1

| Ear Canal Size (mm) | SPLR (sec) |
| --- | --- |
| 6.0 | 3/2/3 |
| 6.4 | 7/4/3 |
| 7.6 | 2/2/3 |
| 8.0 | 3/4/5 |
| 8.1 | 10/12/6 |
| 8.8 | 90/85/33 |

The data in Table 1 show that the earplugs become effective more quickly in smaller ear canals, particularly those 8 mm in diameter or smaller. The average time to seal the ear from noise was 34 seconds with a median of two to three seconds.

EXAMPLE 2

Earplugs prepared as in Example 1 were mechanically compressed as in Example 1 and inserted into a containment device like that shown in FIG. 5 with the tapered sleeves 19 mm long, having various tapered diameters as set forth in Table 2. After storage at 22° C. for 21 days and about 19 months, the earplugs were evaluated for sound pressure level reduction using six subjects with two earplugs tested for each subject. The test subjects' ear canal size and the time for sound pressure level reduction of 10 dB are set forth in Table 2.

TABLE 2

| Ear Canal Size (mm) | Tapered Sleeve Diameter | | SPLR (sec) | |
| --- | --- | --- | --- | --- |
| | Open End | Hemispherical End | Samples aged 21 days | Samples aged 19 months |
| 6.4 | 6.9 | 5.1 | 15/6 | 12/10 |
| 7.6 | 7.2 | 5.5 | 5/2 | 11/8 |
| 7.7 | 7.6 | 5.9 | 61/8 | 5/30 |
| 8.0 | 7.6 | 5.9 | 15/24 | 63/29 |
| 8.1 | 8.0 | 6.4 | 3/2 | 2/2 |
| 8.8 | 8.4 | 6.8 | 8/5 | 6/4 |

The data in Table 2 show an average recovery time to seal the ear from noise of 24 seconds with a median time of five to six seconds for the earplugs aged 21 days. The earplugs aged about 19 months had an average recovery time to seal the ear from noise of 51 seconds with a median time of 10 to 11 seconds. This demonstrates a limited difference in performance between the 21 day aged earplugs and 19 month aged earplugs, with both sample sets performing within the expected 120 second elapsed time period.

EXAMPLE 3

Earplugs were mechanically compressed and placed in the sleeves of a containment device as in Example 2 and aged for 21 days and 19 months at 22° C. The earplugs ranged in size from size 1 to 6 as described in Example 2. The earplugs were removed from the sleeves and tested for sound pressure reduction with two earplugs of each size being tested in a subject having an ear canal 8.8 mm in diameter. The earplug size and the time for a sound pressure level reduction of 10 dB is reported in Table 3.

TABLE 3

| Tapered Sleeve Diameter | | SPLR (sec) | |
| --- | --- | --- | --- |
| Open End | Hemispherical End | Samples aged 21 days | Samples aged 19 months |
| 6.9 | 5.1 | 9/18 | 240/120 |
| 7.2 | 5.5 | 3/10 | 120/9 |
| 7.6 | 5.9 | 13/5 | 5/3 |
| 8.0 | 6.4 | 3/4 | 4/3 |
| 8.4 | 6.8 | 8/5 | 6/4 |
| 8.9 | 7.2 | 2/3 | 3/2 |

The data in Table 3 demonstrates that 23 of the 24 seal times met expectations of 120 seconds with only one of the earplugs aged about 19 months in the smallest tapered sleeve exceeding the 120 second seal time expectation when tested in the ear canal of a person having an 8.8 mm diameter ear canal.

The various modifications and alterations of this invention will be apparent to those skilled ;in the art without departing from the scope and spirit of this invention and this invention should not be restricted to that set forth herein for illustrative purposes.

What is claimed is:

1. A method for forming an earplug containment device comprising providing at least one thin-walled, hollow sleeve having an inside diameter less than the diameter of the human ear canal, compressing a slow-recovery earplug having a diameter greater than that of the human ear canal to a cross-sectional size less than that of said sleeve and inserting said compressed earplug into said sleeve.

2. The method of claim 1 wherein said sleeve is cylindrical.

3. The method of claim 2 wherein said sleeve has an inside diameter of less than about 8 mm.

4. The method of claim 1 wherein said hollow sleeve is tapered with a first end portion being open and having a diameter and a second end portion being hemispherical and having a diameter less than that of said first end portion.

5. The method of claim 4 wherein the diameter of said first end portion is 2 to 3 mm greater than that of said hemispherical end portion.

6. The method of claim 4 wherein the diameter of the open end portion is about 4 to 9 mm.

7. The method of claim 4 wherein said sleeve portion into which said earplug is inserted is at least about 15 mm long.

* * * * *